US012801928B2

(12) United States Patent
Banerjee et al.

(10) Patent No.: US 12,801,928 B2
(45) Date of Patent: Nov. 17, 2026

(54) SPIKING NEURAL NETWORK (SNN) BASED LOW POWER COGNITIVE LOAD ANALYSIS USING ELECTROENCEPHALOGRAM (EEG) SIGNAL

(71) Applicant: Tata Consultancy Services Limited, Mumbai (IN)

(72) Inventors: Dighanchal Banerjee, Kolkata (IN); Sounak Dey, Kolkata (IN); Debatri Chatterjee, Kolkata (IN); Arpan Pal, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 321 days.

(21) Appl. No.: 18/883,943

(22) Filed: Sep. 12, 2024

(65) Prior Publication Data

US 2025/0139442 A1 May 1, 2025

(30) Foreign Application Priority Data

Oct. 26, 2023 (IN) ............................. 202321073014

(51) Int. Cl.
*G06N 3/084* (2023.01)
*A61B 5/00* (2006.01)
(Continued)

(52) U.S. Cl.
CPC ............ *G06N 3/084* (2013.01); *A61B 5/0006* (2013.01); *A61B 5/165* (2013.01); *A61B 5/369* (2021.01);
(Continued)

(58) Field of Classification Search
CPC .......... G06N 3/049; G06N 3/096; G06N 3/08; G06N 3/084; G06N 3/047; A61B 5/372;
(Continued)

(56) References Cited

U.S. PATENT DOCUMENTS

2020/0082735 A1 3/2020 Nel et al.
2024/0273347 A1* 8/2024 Pan ........................ G06N 3/063

OTHER PUBLICATIONS

Yiming et al., ("A Convolutional Spiking Network for Gesture Recognition in Brain-Computer Interfaces" Published 2023 by IEEE. (5 pages) (Year: 2023).*

(Continued)

*Primary Examiner* — Quoc A Tran
(74) *Attorney, Agent, or Firm* — Finnegan, Henderson, Farabow, Garrett & Dunner, LLP

(57) ABSTRACT

State of art techniques, need a decoder following the encoder to encode EEG signals, whose morphology is undefined. Embodiments herein disclose a method and system for a Spiking Neural Network (SNN) based low power cognitive load analysis using electroencephalogram (EEG) signal. The method receives a raw EEG signal from multichannel EEG set up, wherein each of the raw EEG signal is re-referenced and encoded into a spike train using a Light-Weight-Loss-less-Decoder less-Peak-based (LWDLP) encoding. Further, the spike trains are processed by the SNN architecture using backpropagation based supervised approach, wherein the spatial information and the temporal information are learnt by the SNN in form of neuronal activity and synaptic weights. Post learning the SNN architecture applies an activation function on the neuronal activity for classifying a cognitive load level experienced by a subject from among a plurality of predefined cognitive load levels using a SNN classifier.

9 Claims, 5 Drawing Sheets

(51) Int. Cl.

| | |
|---|---|
| ***A61B 5/16*** | (2006.01) |
| ***A61B 5/369*** | (2021.01) |
| ***A61B 5/372*** | (2021.01) |
| ***A61B 5/375*** | (2021.01) |
| ***G06N 3/047*** | (2023.01) |
| ***G06N 3/049*** | (2023.01) |
| ***G06N 3/08*** | (2023.01) |
| ***G06N 3/096*** | (2023.01) |
| ***G16H 40/63*** | (2018.01) |
| ***G16H 40/67*** | (2018.01) |
| ***G16H 50/20*** | (2018.01) |
| ***G16H 50/70*** | (2018.01) |

(52) U.S. Cl.

CPC ............... *A61B 5/372* (2021.01); *A61B 5/375* (2021.01); *A61B 5/7267* (2013.01); *G06F 2218/12* (2023.01); *G06N 3/047* (2023.01); *G06N 3/049* (2013.01); *G06N 3/08* (2013.01); *G06N 3/096* (2023.01); *G16H 40/63* (2018.01); *G16H 40/67* (2018.01); *G16H 50/20* (2018.01); *G16H 50/70* (2018.01)

(58) Field of Classification Search

CPC ....... A61B 5/375; A61B 5/7267; A61B 5/369; A61B 5/165; A61B 5/0006; G16H 40/63; G16H 40/67; G16H 50/20; G16H 50/70; G06F 2218/12

See application file for complete search history.

(56) References Cited

OTHER PUBLICATIONS

Kasabov, Nikola et al., "Spiking neural network methodology for modelling, classification and understanding of EEG spatio-temporal data measuring cognitive processes", Title of the item: Information Sciences, Date: 2014, vol. 295, Publisher: Elsevier, Link: https://kedri.aut.acnz/_data/assets/pdf_file/0010/89578/NK-EC_ISJ.pdf.

Fard, Mojgan Hafezi et al., "Studying Transfer of Learning using a BrainInspired Spiking Neural Network in the Context of Learning a New Programming Language", Date: 2021, Link: https://openrepository.aut.acnz/server/api/core/bitstreams/8a8410a9-1e42-4156-8229-71d2251e6606/content.

Sarlija, Tan C. et al., "NeuroSense: Short-Term Emotion Recognition and Understanding Based on Spiking Neural Network Modelling of Spatio-Temporal EEG Patterns", Title of the item: Neurocomputing, Date: 2021, vol. 434, Link: https://pure.ulster.acuk/ws/files/88807176/NEUCOM_pre_proofs.pdf.

Friedman, Nir et al., "EEG-Based Prediction of Cognitive Load in Intelligence Tests", Title of the item: Frontiers in Human Neuroscience, Date: 2019, Publisher: PubMed, Link: https://www.ncbi.nlm.nih.gov/pmc/articles/PMC6580143/pdf/fnhum-13-00191.pdf.

Banerjee, Dighanchal et al., "An SNN Based ECG Classifier for Wearable Edge Devices", Title of the item: Workshop on Learning from Time Series for Health, Date: 2022, Publisher: NeurIPS 2022 Link: https://openreview.net/pdf?id=V8yemRAs00-#:~:text=Feed%2Dforward%20SNN%20cou%2D%20pled,and%20thus%20minimal%20power%20consumption.

Ledinauskas, Eimantas et al., "Training Deep Spiking Neural Networks", Date: 2020, Link: https://arxiv.org/pdf/2006.04436.

* cited by examiner

SPIKING NEURAL NETWORK (SNN) BASED LOW POWER COGNITIVE LOAD ANALYSIS USING ELECTROENCEPHALOGRAM (EEG) SIGNAL

PRIORITY CLAIM

This U.S. patent application claims priority under 35 U.S.C. § 119 to: India application No. 202321073014, filed on Oct. 26, 2023. The entire contents of the aforementioned application are incorporated herein by reference.

TECHNICAL FIELD

This disclosure relates generally to the field of automated cognitive load analysis and, more particularly, to a method and system for a Spiking Neural Network (SNN) based low power cognitive load analysis using electroencephalogram (EEG) signal, in accordance with some embodiments of the present disclosure.

BACKGROUND

Cognitive load (CL) is the amount of mental workload experienced by an individual while performing a task. User performance is dependent on the CL experienced by the individual. Study reveals that excessive CL might lead to conditions such as stress/anxiety, depression, elevated heart rate, loss of attention/engagement level etc., leading to degradation in performance. However, it is also observed that an optimum amount of CL is required to successfully perform the task. Thus, assessment of CL is important, and research reveals it is a value add while in various application areas such as human behavior analysis, brain-computer interfaces (BCI), adaptive learning etc. For practical use cases, CL computation needs to be done in real time and on device. Conventionally, various physiological changes, controlled by sympathetic and para-sympathetic nervous system, like cardiovascular changes, galvanic skin resistance, eye movements and the like have been used for assessment of CL. However, the most reliable assessment is done using brain signals. Acquiring brain signals using electroencephalogram (EEG) is relatively easier and cheaper compared to functional magnetic resonance imaging (fMRI).

Thus, attempts have been made to use EEG based measurements in real life scenarios. EEG band powers like theta, alpha and beta band powers, reflect the CL. For problem solving tasks, researchers have used alpha power and asymmetry in alpha band as features. Literature suggests that theta activity in hippocampus area is associated with cognitive performance. Various machine learning (ML) and deep learning (DL) approaches have been used in studies for assessment, classification and prediction of CL. Deep learning based architectures offer better classification accuracy compared to machine learning models, but they require large volumes of data for training and learning the feature representation. Additionally, more accurate and high-performance models involve a large number of network parameters, which in turn calls for more complex computations and power consumption.

Moreover, EEG signals are highly susceptible to various artifacts like muscle artifacts, blink artifacts, movement artifacts, jaw movements etc. Thus, noise removal is a necessary step in EEG signal processing which also calls for additional computations. Thus, it is still a challenge to use EEG for real time CL analysis on wearable EEG devices itself.

Recently, Spiking Neural Networks (SNNs), a next-gen ML framework has been developed inspired by functionalities of neurons and synapses of mammalian brain. SNNs run on non-von Neumann Neuromorphic Computing (NC) platforms such as Intel Loihi™, Brainchip Akida™ etc., and are capable of low power computations using sparser data. Thus, these are an eligible candidate for implementing machine intelligence at battery driven edge devices (like robots, wearable etc.), which have low compute resource. Features such as (i) event based asynchronous data processing in form of spikes, (ii) collocation of memory and compute in spiking neurons, and (iii) natural ability of temporal feature extraction, makes SNN-NC combo to be inherently very low-power and low-compute approach particularly fit for CL analysis on wearable EEG devices.

However, the SNN architecture design is critical to achieve all or most of the above advantages of SNN. Thus, exploring techniques to reduce power consumption during EEG analysis for real time application on edge devices with due consideration that EEG signals are noisy signals is an open area of research.

SUMMARY

Embodiments of the present disclosure present technological improvements as solutions to one or more of the above-mentioned technical problems recognized by the inventors in conventional systems.

For example, in one embodiment, a method for a Spiking Neural Network (SNN) based low power cognitive load analysis using electroencephalogram (EEG) signal is provided.

The method includes receiving a raw electroencephalogram (EEG) signal of a subject from a multichannel EEG set up for an observation window, wherein the subject is under continuous observation. The raw EEG signal is re-referenced to generate a re-referenced EEG signal of each channel using average of channels as reference. Further, the method includes simultaneously applying a Light-Weight-Lossless-Decoder less-Peak-based (LWDLP) encoding technique on the re-referenced EEG signal of each channel of the multichannel EEG set up to generate a spike train to be consumed by the SNN architecture, the LWLDP encoding technique comprising: (a) detecting a plurality of peaks in the re-referenced EEG signal using slope of the EEG signal in the time domain; and (b) assigning a spike at each time instant associated with each peak among the plurality of detected peaks and generate the spike train by retains temporal information of the re-referenced EEG signal by making the inter-spike interval equal to inter-peak interval and retaining spatial information by encoding peaks as spikes.

Furthermore, the method includes classifying a cognitive load level of the subject by processing the spike train generated for each channel by the SNN architecture comprising, a spiking network implemented using one of a reservoir and a feed forward SNN, followed by a SNN classifier, wherein the reservoir or the feed forward SNN is selected in accordance with hardware constraints of an edge device, wherein the SNN architecture learns using back-propagation based supervised approach, wherein the spatial information and the temporal information are learnt by the SNN in form of neuronal activity and synaptic weights, and wherein post learning the SNN architecture applies an activation function on the neuronal activity for classifying the cognitive load level of the subject from among a plurality of predefined cognitive load levels using the SNN classifier.

In another aspect, a system for a Spiking Neural Network (SNN) based low power cognitive load analysis using electroencephalogram (EEG) signal is provided. The system comprises a memory storing instructions; one or more Input/Output (I/O) interfaces; and one or more hardware processors coupled to the memory via the one or more I/O interfaces, wherein the one or more hardware processors are configured by the instructions to receive a raw electroencephalogram (EEG) signal of a subject from a multichannel EEG set up an observation window, wherein the subject is under continuous observation. The raw EEG signal is re-referenced to generate a re-referenced EEG signal of each channel using average of channels as reference. Further, the system is configured to simultaneously apply a Light-Weight-Lossless-Decoder less-Peak-based (LWDLP) encoding technique on the re-referenced EEG signal of each channel of the multichannel EEG set up to generate a spike train to be consumed by the SNN architecture, the LWLDP encoding technique comprising: (a) detecting a plurality of peaks in the re-referenced EEG signal using slope of the EEG signal in the time domain; and (b) assigning a spike at each time instant associated with each peak among the plurality of detected peaks and generate the spike train by retains temporal information of the re-referenced EEG signal by making the inter-spike interval equal to inter-peak interval and retaining spatial information by encoding peaks as spikes.

Furthermore, the system is configured to classify a cognitive load level of the subject by processing the spike train generated for each channel by the SNN architecture comprising, a spiking network implemented using one of a reservoir and a feed forward SNN, followed by a SNN classifier, wherein the reservoir or the feed forward SNN is selected in accordance with hardware constraints of an edge device, wherein the SNN architecture learns using back-propagation based supervised approach, wherein the spatial information and the temporal information are learnt by the SNN in form of neuronal activity and synaptic weights, and wherein post learning the SNN architecture applies an activation function on the neuronal activity for classifying the cognitive load level of the subject from among a plurality of predefined cognitive load levels using the SNN classifier.

In yet another aspect, there are provided one or more non-transitory machine-readable information storage mediums comprising one or more instructions, which when executed by one or more hardware processors causes a method for a method for a Spiking Neural Network (SNN) based low power cognitive load analysis using electroencephalogram (EEG) signal is provided.

The method includes receiving a raw electroencephalogram (EEG) signal of a subject from a multichannel EEG set up an observation window, wherein the subject is under continuous observation. The raw EEG signal is re-referenced to generate a re-referenced EEG signal of each channel using average of channels as reference. Further, the method includes simultaneously applying a Light-Weight-Lossless-Decoder less-Peak-based (LWDLP) encoding technique on the re-referenced EEG signal of each channel of the multichannel EEG set up to generate a spike train to be consumed by the SNN architecture, the LWLDP encoding technique comprising: (a) detecting a plurality of peaks in the re-referenced EEG signal using slope of the EEG signal in the time domain; and (b) assigning a spike at each time instant associated with each peak among the plurality of detected peaks and generate the spike train by retains temporal information of the re-referenced EEG signal by making the inter-spike interval equal to inter-peak interval and retaining spatial information by encoding peaks as spikes.

Furthermore, the method includes classifying a cognitive load level of the subject by processing the spike train generated for each channel by the SNN architecture comprising, a spiking network implemented using one of a reservoir and a feed forward SNN, followed by a SNN classifier, wherein the reservoir or the feed forward SNN is selected in accordance with hardware constraints of an edge device, wherein the SNN architecture learns using back-propagation based supervised approach, wherein the spatial information and the temporal information are learnt by the SNN in form of neuronal activity and synaptic weights, and wherein post learning the SNN architecture applies an activation function on the neuronal activity for classifying the cognitive load level of the subject from among a plurality of predefined cognitive load levels using the SNN classifier.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

Figure 1A:
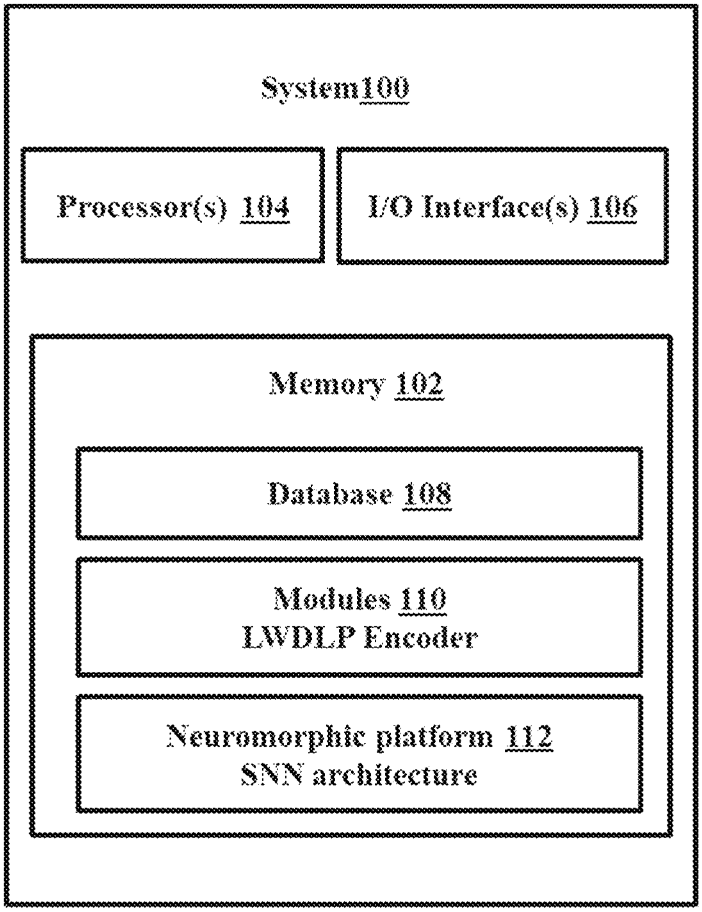
FIG. 1A is a functional block diagram of a system for a Spiking Neural Network (SNN) based low power cognitive load analysis using electroencephalogram (EEG) signal, in accordance with some embodiments of the present disclosure.

It should be appreciated by those skilled in the art that any block diagrams herein represent conceptual views of illustrative systems and devices embodying the principles of the present subject matter. Similarly, it will be appreciated that any flow charts, flow diagrams, and the like represent various processes which may be substantially represented in computer readable medium and so executed by a computer or processor, whether or not such computer or processor is explicitly shown.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

State of the art methods have researched on usage of Spiking Neural Network SNN for analysis of physiological signals such as electroencephalogram (EEG) and electrocardiogram (ECG).

One of the requirements of SNN is encoding these signals into a spike train for the SNN to process it for desired prediction. The encoding techniques used by state-of-the-art approaches require a decoder that provides a feedback for encoder to learn and improve on encoding accuracy. Addition of a module adds to space and computation complexity.

Further encoding of the ECG signal is technically less challenging as the ECG signal has a fixed morphology with waveform pattern following P,Q,R,S,T wave in a sequential manner and the temporal relation is predefined. This known temporal relation enables to easily express those waveforms as spikes, but in case of EEG that is not the case. There is no known morphology that helps in understanding the EEG signal. What to encode and how to encode is not trivial in ECG encoding unlike EEG which has no defined pattern in space, time, and amplitude, further inherently is very noisy due to impact of artifacts such as blink artifacts, muscle artifacts and the like. This demands preprocessing or enhanced encoding techniques. This is one of the challenges of EEG analysis in real time applications on edge devices Thus, general state of art approaches that utilize SNN for EEG analysis require a decoder loop to ensure encoder learns with objective of improving encoding to capture maximum information, effectively improving the output analysis of SNNs. However, decoder adds additional computational burden on an edge device with power constraints or hardware constraints and existing SNN architectures have challenge for being used in real time analysis if EEG on edge devices.

Embodiments herein disclose a method and system for a Spiking Neural Network (SNN) based low power cognitive load analysis using electroencephalogram (EEG) signal. The method receives a raw EEG signal from multichannel EEG set up, wherein each raw EEG signal after re-referencing is encoded into a spike train using a Light-Weight-Lossless-Decoder less-Peak-based (LWDLP) encoding. Further, the spike trains are processed by the SNN architecture using backpropagation based supervised approach, wherein the spatial information and the temporal information are learnt by the SNN in form of neuronal activity and synaptic weights. Post learning the SNN architecture applies an activation function on the neuronal activity for classifying a cognitive load level experienced by a subject from among a plurality of predefined cognitive load levels using a SNN classifier.

The encoding techniques mentioned in the state-of-the-art SNN based EEG analysis approaches either do not depend on the nature and size of the data or do not ensure the retention of information content in the spike trains i.e., they are lossy encoding techniques. The LWDLP encoding technique used by the method disclosed is not lossy and takes care of the above-mentioned technical challenges.

The enhancement of data representation in spike trains using error optimization techniques are also limited to the encoding algorithms that have a decoder part with it (such as HSA, BSA, TC etc.). But that is not the case with the current proposed invention. It does not require a decoder part of the encoder for the SNN to learn the spike trains created from EEG data.

Also, the encoding mechanism used in the earlier works are mostly rate based. Whereas the proposed invention uses a encoding method that is capable of retaining the temporal signature of the data. The temporal way of encoding data works better than the rate-based method.

In the LWDLP encoding technique herein, a simple technique has been used to check for the peaks in the signal based on a particular threshold value and the slope of the signal at those particular points. In this case, no morphology of the structured data (like EEG) is considered. The spike encoder automatically creates a spike train by preserving the temporal pattern of the signal and in turn the information content of the data. It is also to be noted that the encoding technique does not bring in much computational overhead as it is based on threshold only, not on any complex mathematical computation.

Also, since each channel of the EEG signal is represented by a separate spike train, there is no possibility of spatial overlapping, making the proposed invention more generic and information preserving. This aspect of the encoding is not always taken care of in the existing methods.

Referring now to the drawings, and more particularly to FIGS. 1A through 3, where similar reference characters denote corresponding features consistently throughout the figures, there are shown preferred embodiments, and these embodiments are described in the context of the following exemplary system and/or method.

FIG. 1A is a functional block diagram of a system 100 for a Spiking Neural Network (SNN) based low power cognitive load analysis using raw electroencephalogram (EEG) signal, in accordance with some embodiments of the present disclosure.

In an embodiment, the system 100 provides a neuromorphic platform 112, deployed with the SNN architecture. The SNNs run on non-von Neumann Neuromorphic Computing (NC) platforms such as Intel Loihi™, Brainchip Akida™ etc., and are capable of low power computations using sparser data.

Further, the system 100 includes a processor(s) 104, communication interface device(s), alternatively referred as input/output (I/O) interface(s) 106, and one or more data storage devices or a memory 102 operatively coupled to the processor(s) 104. The system 100 with one or more hardware processors is configured to execute functions of one or more functional blocks of the system 100.

Referring to the components of system 100, in an embodiment, the processor(s) 104, can be one or more hardware processors 104. In an embodiment, the one or more hardware processors 104 can be implemented as one or more microprocessors, microcomputers, microcontrollers, digital signal processors, central processing units, state machines, logic circuitries, and/or any devices that manipulate signals based on operational instructions. Among other capabilities, the one or more hardware processors 104 are configured to fetch and execute computer-readable instructions stored in the memory 102. In an embodiment, the system 100 can be implemented in a variety of computing systems including laptop computers, notebooks, hand-held devices such as mobile phones, edge devices such as battery operated wearable devices, robotic agents that have hardware constraints for execution high computational tasks. However, the system 100 can also be implemented in devices such as workstation, mainframe computers, servers, and the like.

The I/O interface(s) 106 can include a variety of software and hardware interfaces, for example, a web interface, a graphical user interface and the like and can facilitate multiple communications within a wide variety of networks N/W and protocol types, including wired networks, for example, LAN, cable, etc., and wireless networks, such as WLAN, cellular and the like. In an embodiment, the I/O interface(s) 106 can include one or more ports for connecting to a number of external devices or to another server or devices.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes.

In an embodiment, the memory 102 includes a plurality of modules 110 such as Light-Weight-Lossless-Decoder less-Peak-based (LWDLP) encoder for generating a spike train from raw EEG signal, after referencing, to be consumed by the SNN architecture.

The plurality of modules 110 include programs or coded instructions that supplement applications or functions performed by the system 100 for executing different steps involved in the process of cognitive load analysis, being performed by the system 100. The plurality of modules 110, amongst other things, can include routines, programs, objects, components, and data structures, which performs particular tasks or implement particular abstract data types. The plurality of modules 110 may also be used as, signal processor(s), node machine(s), logic circuitries, and/or any other device or component that manipulates signals based on operational instructions. Further, the plurality of modules 110 can be used by hardware, by computer-readable instructions executed by the one or more hardware processors 104, or by a combination thereof. The plurality of modules 110 can include various sub-modules (not shown).

Further, the memory 102 may comprise information pertaining to input(s)/output(s) of each step performed by the processor(s) 104 of the system 100 and methods of the present disclosure.

Further, the memory 102 includes a database 108. The database (or repository) 108 may include a plurality of abstracted pieces of code for refinement and data that is processed, received, or generated as a result of the execution of the plurality of modules in the module(s) 110.

Although the data base 108 is shown internal to the system 100, it will be noted that, in alternate embodiments, the database 108 can also be implemented external to the system 100, and communicatively coupled to the system 100. The data contained within such an external database may be periodically updated. For example, new data may be added into the database (not shown in FIG. 1A) and/or existing data may be modified and/or non-useful data may be deleted from the database. In one example, the data may be stored in an external system, such as a Lightweight Directory Access Protocol (LDAP) directory and a Relational Database Management System (RDBMS).

Figure 1B:
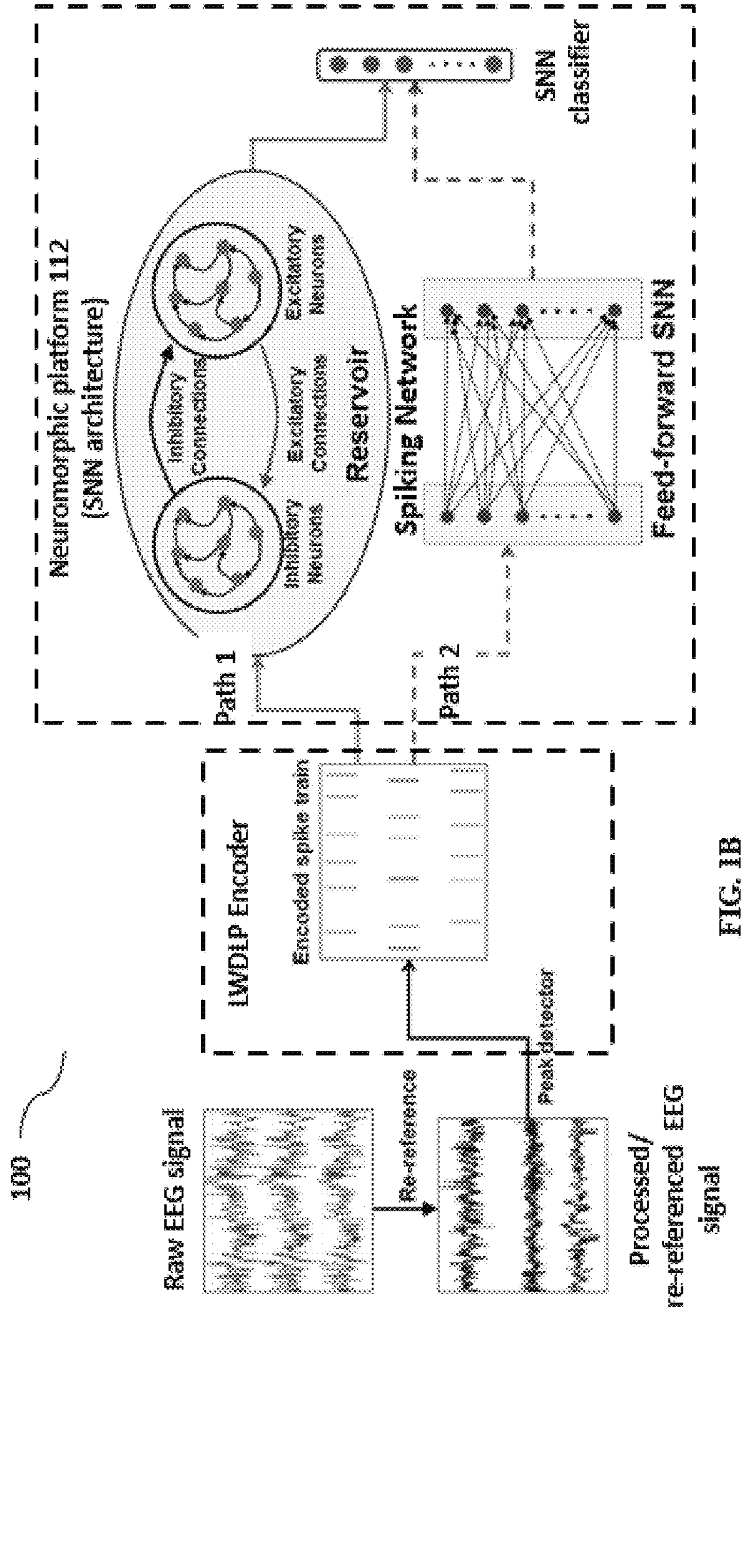
FIG. 1B illustrates an architectural overview of the system of FIG. 1A, in accordance with some embodiments of the present disclosure.

The neuromorphic platform 112 is implemented based on a SNN architecture. The SNN architecture has two main sub-system namely 'Spike Converter' (not shown explicitly) and 'Neuromorphic Accelerator' (not shown explicitly). A neuromorphic accelerator in general is a hardware accelerator specifically designed to run Graph like architectures or Neural Networks like architectures (operating in event domain) at very-low power. These neuromorphic accelerators have BUS connectivity to existing sub-systems like the CPU and the memory controllers, in order to take input data, then process it and return the output. Further, as depicted in FIG. 1B, the SNN architecture SNN comprises a spiking network followed by a SNN classifier. The spiking network can be one of a reservoir or the feed forward SNN, which is selected in accordance with hardware constraints of an edge device, such as a wearable device, where the system 100 is to be deployed for cognitive load analysis.

Functions of the components of the system 100 are now explained with reference to steps in flow diagrams in FIG. 1B through FIG. 3.

FIG. 1B illustrates an architectural overview of the system 100 of FIG. 1A, in accordance with some embodiments of the present disclosure and is further explained in conjunction with the flow diagram of FIG. 2.

Figure 2A:
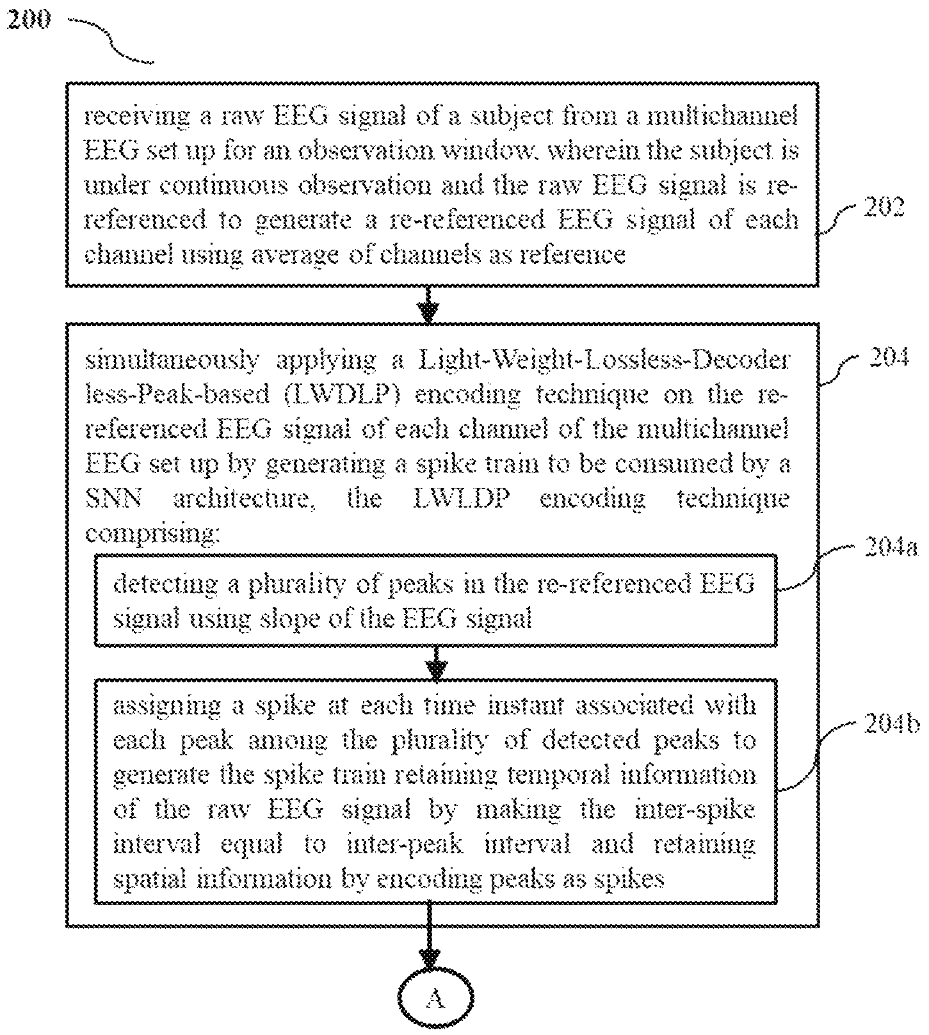
FIGS. 2A through 2B (collectively referred as FIG. 2) is a flow diagram illustrating a method for SNN based low power cognitive load analysis using EEG signal, using the system depicted in FIGS. 1A and 1B, in accordance with some embodiments of the present disclosure.
Figure 2B:
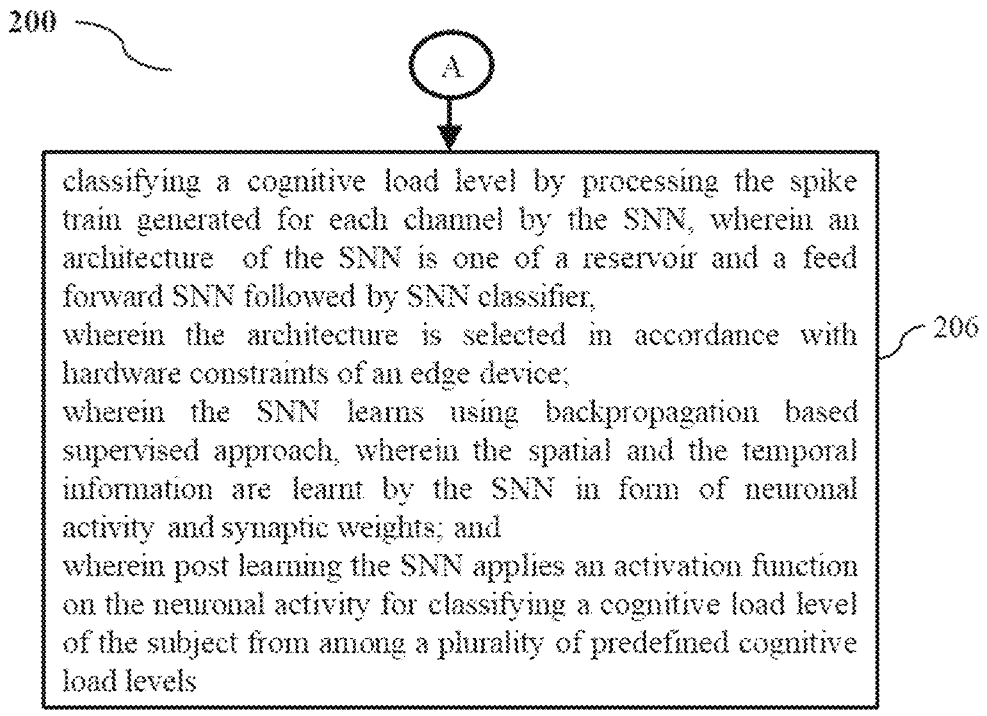

FIGS. 2A through 2B (collectively referred as FIG. 2) is a flow diagram illustrating a method 200 for the Spiking Neural Network (SNN) based low power cognitive load analysis using raw electroencephalogram (EEG) signal, using the system depicted in FIGS. 1A and 1B, in accordance with some embodiments of the present disclosure.

In an embodiment, the system 100 comprises one or more data storage devices or the memory 102 operatively coupled to the processor(s) 104 and is configured to store instructions for execution of steps of the method 200 by the processor(s) or one or more hardware processors 104. The steps of the method 200 of the present disclosure will now be explained with reference to the components or blocks of the system 100 as depicted in FIGS. 1A and 1B and the steps of flow diagram as depicted in FIG. 2. Although process steps, method steps, techniques or the like may be described in a sequential order, such processes, methods, and techniques may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

Referring to system architecture in FIG. 1B and the steps of the method 200, at step 202 of the method 200, the one or more hardware processors 104 are configured by the instruction to receive a raw electroencephalogram (EEG) signal of a subject from a multichannel EEG set up for an observation window, wherein the subject is under continuous observation. Moreover, EEG signals are highly susceptible to various artifacts like muscle artifacts, blink artifacts, movement artifacts, jaw movements etc. Thus, noise removal is a necessary step in EEG signal processing which also calls for additional computations. Thus, it is still a challenge to use EEG for real time Cognitive Load (CL) analysis on wearable EEG devices itself. Artifacts removal is a compulsory step for EEG analysis. However the method disclosed does not need this process, utilizes EEG signal as acquired from electrodes and can provide satisfactory results for EGG signals with and without artifacts, and can be seen later in experimental analysis and results section. EEG recordings measure the difference in electrical potential of each electrode with respect to a reference electrode. To represent voltage in each of the channels with respect to another electrode, the channels are re-referenced. This new reference can be any particular channel, or the average of a channels. Herein, the average of a channel is used as reference. This provides a re-referenced signal (processed EEG data) as can been seen in FIG. 1B.

At step 204 of the method 200, the one or more hardware processors 104 are configured by the instruction to simultaneously apply, via the LWLDP encoder depicted in FIGS. 1A and 1B, the Light-Weight-Lossless-Decoder less-Peak-based (LWDLP) encoding technique on the re-referenced EEG signal of each channel of the multichannel EEG set up, to generate a spike train to be consumed by the SNN architecture of the neuromorphic platform 112.

Figure 3:
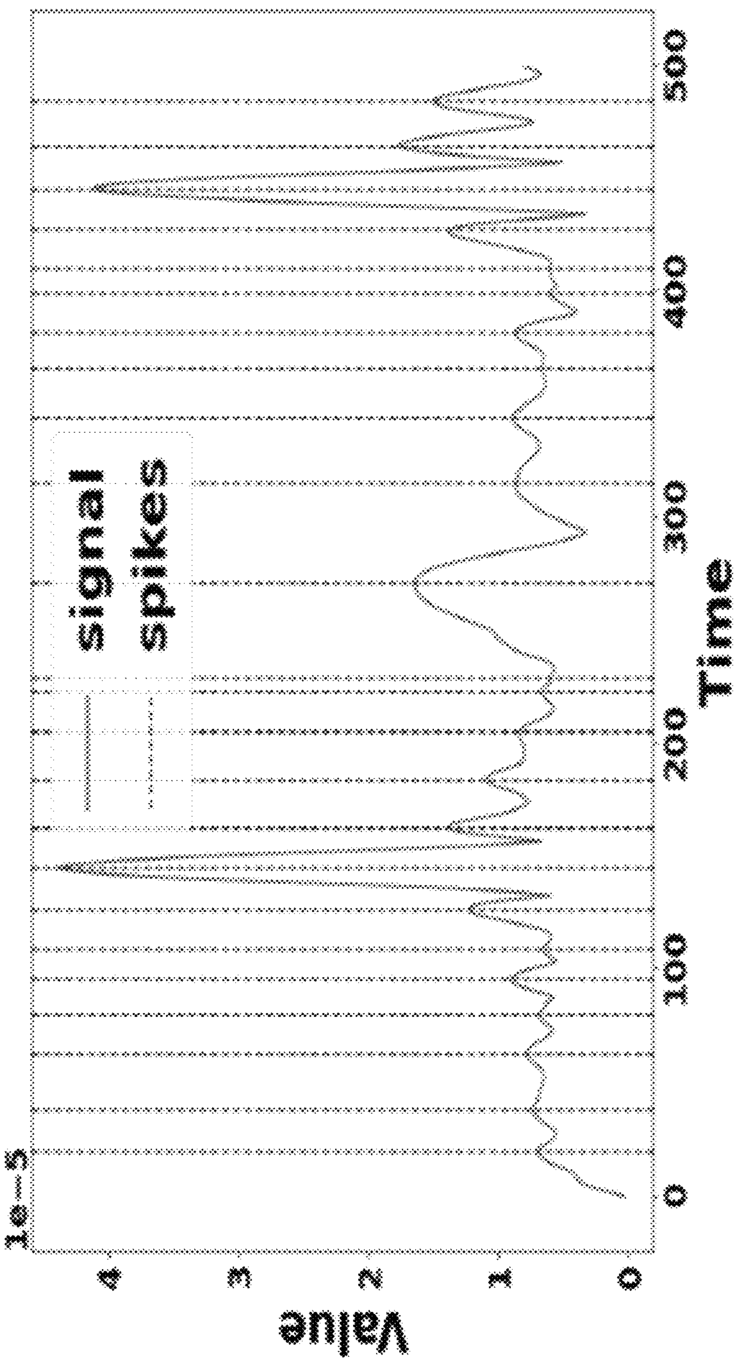
FIG. 3 depicts peak-based spike encoding of a raw EEG signal using a Light-Weight-Lossless-Decoder less-Peak-based (LWDLP) encoder of the system, in accordance with some embodiments of the present disclosure.

Any real-life analog data, such as EEG signal, need to be converted into a train of events, aka spikes, because SNNs can work on events or spikes only. The spikes carry the signal information to other neurons in the network. The information may be coded via the number of spikes or via inter-spike interval. The method disclosed uses peaks of all the re-referenced EEG channels and considers them as spikes (LWDLP encoding). In the LWDLP encoding technique herein, a simple technique has been used to check for the peaks in the signal based on a particular threshold value and the slope of the signal at those particular points. A small window of the raw EEG signal is observed to check how the EEG signal is changing over the time t. If the change is over a threshold for both t−1 to t and t to t+1, then the system 100 proceeds with the next steps of peaks detection. The threshold is a hyperparameter which is set according to the range of the EEG data. This way, the spike train retains the temporal pattern of the EEG signal. A representative diagram of a single EEG channel and corresponding spike train are depicted in FIG. 3.

The LWLDP encoding technique:

1. Detects a plurality of peaks in the re-referenced EEG signal using slope of the EEG signal in the time domain (204*a*).
2. Assigns a spike at each time instant associated with each peak among the plurality of detected peaks, if the peak is above a predefined threshold, to generate the spike train retaining temporal information of the re-referenced EEG signal by making the inter-spike interval equal to inter-peak interval and retaining spatial information by encoding peaks as spikes (204*b*).

It can be noted that LWDLP encoding technique captures the spatial and temporal information directly from the re-referenced EEG signal without requiring any preprocessing, and the there is no need of feature extraction process required. This is one factor in reducing computation of the overall system. Furthermore, it is observed that the spike train generated by the LWDLP encoder using peak based approach based on threshold provides fairly accurate encoding, and unlike state of the art spike generation approaches used specifically for EEG, the LWDLP encoder disclosed does not require a decoder for the encoder to learn for the errors. This is another major factor that reduces computational complexity of the overall system making is appropriate choice for deployment on edge devices having target constraints such as memory, power constraints and the like.

Once the spike train is generated for each channel EEG signal, then at step 206 of the method 200, the one or more hardware processors 104 are configured by the instruction to process the spike train generated for each channel by the SNN architecture. In one embodiment the spiking network can be the reservoir and in another embodiment the spiking network can be a feed forward SNN and is selected based on hardware constraints of an edge device, where the system 100 is to be deployed. The selection of the reservoir or the feed forward SNN is in accordance with hardware constraints of an edge device, such as a wearable device or robotic agent, where the system 100 is deployed. The reservoir is a much more complex, computation and memory hungry architecture compared to feed forward. But essentially reservoir being a recurrent connection based architecture, it is supposed to understand the temporal relation within the signal better. But in doing so, it is spending a lot of SOP and power. If the edge device can afford to accommodate such architecture, then reservoir is selected. Otherwise the feed forward SNN, which is a light weight model which can definitely fit in the edge device or any neuromorphic chips.

The final block of the SNN architecture is the SNN classifier that follow the spiking network. The SNN architecture learns using backpropagation based supervised approach, wherein the spatial information and the temporal information captured in the spike train are learnt by the SNN in form of neuronal activity and synaptic weights.

Post learning the SNN architecture applies an activation function on the neuronal activity for classifying a cognitive load level of the subject from among a plurality of predefined cognitive load levels using the SNN classifier. In one implementation the activation function is a sigmoid function. The alternative implementations, the activation function such as ReLu, Softmax can be used. However, sigmoid is preferred for binary & multi-label classification problems whereas Softmax is preferred for multi-class classification problems where the model is expected to "pick a class". ReLu also suffers from the problem of overfitting due to faster convergence. The main reason for selecting the sigmoid function is because it exists between (0 to 1). Therefore, it is especially used for models where it is intended to predict the probability as an output. Since probability of anything exists only between the range of 0 and 1, sigmoid is the right choice. The number of output neurons in a last layer of the SNN classifier corresponds to the number of classes associated with the plurality of predefined cognitive load levels.

As can be seen in FIG. 1, the system 100 utilizes one of the two SNN architectures a recurrent (in the form of reservoir) and another is the feed-forward SNN. The recurrent network is expected to capture the temporal signature of EEG signal better, whereas the feed-forward network is easier to implement on NC platforms.

The reservoir: The reservoir is a set of excitatory and inhibitory spiking neurons that are recurrently connected. The inter-neuron synaptic connectivity, however, is sparse, probabilistic and remain within the same population to ensure dynamical stability of the network. This kind of recurrently connected set of neurons are very efficient in extracting spatial and temporal information from temporally varying signals such as EEG. Recurrent weights with directed cycles do play the role of a non-linear random projection of the sparse input feature space into a higher dimensional spatio-temporal embedding—and that helps generating explicit temporal features.

The feed forward SNN: It is a simple network topology where the spiking neurons connected across consecutive layers but usually there is no intra-layer connection. Herein the system 100 utilizes full connectivity between layers. Once the input spike train is fed into the network, these connections learn via Backpropagation rule. Post training, the network captures the learned features in neuronal activities and synaptic weights. The architectures above and different parameters used in them can are in accordance with work proposed by Dey et al., 2022. A Leaky-Integrate and Fire (LIF) neuron model known in the art is used to implement aforesaid SNNs. LIF is computationally easier to simulate and work with compared to other neuron models such as Izhikevich, McCulloch-Pitts etc. In LIF model, the membrane potential of a neuron decays according to its temporal dynamics and is incremented with the incoming inputs. If the membrane potential of a neuron crossed a certain fixed threshold, the neuron emits a spike. After spiking, a neuron goes into a refractory period and in this period, the neuron does not receive any incoming data and acts as a dead neuron. LIF neuron model is described below:

$$\tau_m \frac{dV}{dt} = (V_{rest} - V) + IR \quad (1)$$

$$s = \begin{cases} 1, & V \geq V_{thresh} \\ 0, & V < V_{thresh} \end{cases}$$

In the equation 1, V is the neuron membrane potential that varies with the input stimuli and when it crosses a threshold, $V_{thresh}$, the neuron emits a spike s. $V_{rest}$ is the resting membrane potential, I represents the total input current to the neuron from all its synapses. R is the total resistance encountered by I during synaptic transmission. Without any input, V exponentially decays with a time constant $T_m$.

Classification: In one implementation a sigmoid function on the membrane potentials of output layer neurons to get the final classification results. In the system 100 the number of output neurons always corresponds to the number of classes available for the task in hand.

Experimental Results and Discussion:

Dataset description: Two publicly available datasets, namely MIT-PhysioNet EEGMAT [Zyma et al., 2019] and Simultaneous Task EEG Workload (STEW) [44r, 2018] are used for experimental analysis of the system 100. EEGMAT dataset contains artifacts free signals of 36 subjects performing mental arithmetic tasks. EEG signals were recorded using 23-channel EEG device (sampling frequency 500 Hz.) for 3 minutes of resting state and 1 minute of task period. The participants were divided into Group "B" and Group "G" based on their performance. Participants belonged to Group "B", who faced difficulty in performing the task. The remaining participants belonged to Group "G". STEW dataset contains raw signals of subjects for SIMKAP multitasking test. The signals were captured using a 14 channel Emotiv™ device (sampling frequency of 128 Hz). EEG data was acquired for 2.5 minutes with subjects at rest. Next, subjects performed the SIMKAP test and the final 2.5 minutes were used as the workload condition. Subjects rated their perceived Cognitive Load (CL) after each segment of the experiment on a scale of 1-9.

Data Preparation: EEGMAT contains artifacts free EEG data and STEW dataset contains EEG data with artifacts. Artifacts removal is a compulsory step for EEG analysis. However, herein the method does not require this step, and EEG signals are used as is (raw EEG signals). EEG recordings measure the difference in electrical potential of each electrode with respect to a reference electrode. To represent voltage in each of the channels with respect to another electrode, the channels are re-referenced as depicted in FOG. 1B. This new reference can be any particular channel, or the average of a channels. The average of a channel is used as reference. Next, the peaks are detected in this re-referenced signal using the NeuroKit™ toolbox [Makowski et al., 2021]. Thus, a train of spikes for a EEG signal is obtained. Next, a window of length w see are selected which are then used to train the SNN network. Experiments are conducted with various window sizes to see its effect on performance. To mitigate the class imbalance problem in both the datasets, the EEG data is down sampled. The spiking networks of FIG. 1B are designed and simulated via snnTorch™—a PyTorch™ based SNN simulator [Eshraghian et al., 2021]. A tool called RayTune™ [Liaw et al., 2018] has been used for hyper parameter tuning. Different sets of network parameters were used for experiments. Among those sets of network parameters, the optimal set was found using a grid-search method using RayTune. The parameter values used for both reservoir and feed-forward 156 network architectures are listed in Table 1.

TABLE 1

Network parameters for the experiments

| | Reservoir | | | | | Feed-Forward | |
|---|---|---|---|---|---|---|---|
| Dataset | No. of excitatory neurons | No. of inhibitory neurons | Input Outdegree | Weight Scalar | $T_m$ | No. of feed forward neurons | $T_m$ |
| EEGMAT | 4000 | 1000 | 500 | (2.0, 1.7, 0.9, 0.1, 1.4) | 15 | 2000 | 20 |
| STEW | 5000 | 1000 | 500 | (2.0, 1.4, 0.3, 0.7, 1.1) | 25 | 4000 | 30 |

With these optimal set of parameters, two different types of testing methodologies were executed-(a) Classical 5-fold cross validation (5-FCV) and (b) Leave-One-Subject-Out (LOSO). In the 5-FCV method, training and testing was performed using a 80-20 split. The EEGMAT has two classes while STEW has three classes. A window size w=1, 2 and 4 seconds is used for both the cases. The results are summarized below.

The State of the Art (SoA) methods are as below:

[1]: [Ramaswamy et al., 2021], [2]: [Siddhad et al., 2022], [3]: [Pandey et al., 2020], and [4]: [Attallah, 2020]

TABLE 2

| | Accuracy (%) | | |
|---|---|---|---|
| Dataset | SoA | System 100 | SOP |
| EEGMAT | 95 [1] | 70 | 8 |
| STEW | 88 [2] | 64 | 25 |

Table 2 reports the performance of the Reservoir network on both the datasets using 5-FCV testing methodology and a window size of 2 seconds. The system 100 achieved less accuracy compared to state of the arts (SoA). Moreover, the computational cost is found to be high for the Reservoir. To understand the computational cost quantitatively, with Synaptic Operations (SOP) as a metric. Usually, number of SOP is considered as the average number of spikes per timestep for the entire training and inference and more spikes means more computation. The last column of Table 2 shows the estimate of SOP per timestep for both the datasets. Due to recurrent connections between large number of neurons in the reservoir (refer Table 1), large number of SOP was observed in the network resulting in higher computation cost and processing time.

Table 3 reports performance of feed-forward network for both 5-FCV and LOSO methods with respect to different window sizes. It is observed that the classification accuracy varies with window size. Window size=2 seconds provides the best performance-75% & 86% (5 FCV) and 70% & 79%. (LOSO) classification for EEGMAT and STEW respectively. Respective F1 scores are also reported 175 in the table. For EEGMAT, a smaller window size (1 second), degrades the performance for both LOSO and 5-FCV, whereas increasing window size from 2 seconds to 4 seconds degrades LOSO performance but does not affect much for 5-FCV. For STEW, degradation is observed for both the cases.

TABLE 3

| Dataset | Window size (w) (second) | Input spikes per window of EEG data | Feed Forward SNN 5-FCV Accuracy | 5-FCV F1 score | LOSO Accuracy | LOSO F1 score |
|---|---|---|---|---|---|---|
| EEGMAT | 1 | 22 | 68 | 0.73 | 60 | 0.63 |
| | 2 | 45 | 75 | 0.76 | 70 | 0.72 |
| | 4 | 92 | 75 | 0.74 | 55 | 0.56 |
| STEW | 1 | 25 | 84 | 0.84 | 77 | 0.77 |
| | 2 | 52 | 86 | 0.87 | 79 | 0.80 |
| | 4 | 104 | 80 | 0.79 | 71 | 0.71 |

Table 4 reports the performance comparison between existing SoA and feed-forward SNN. Clearly for LOSO testing method, the system 100 performs better with respect to the LSTM based approach [Pandey et al., 2020] and at par with SVM-KNN based approach [Attallah, 2020]. For 5-FCV, the system 100 performs at par for STEW dataset compared to a transformer based architecture [Siddhad et al., 2022]. For EEGMAT the accuracy is less compared to that reported in [Ramaswamy et al., 2021], which used a combination of topographic map generation and Conv-LSTM model. LOSO being a more generic and acceptable testing method, the system 100 seems fit for practical applications. However, the real benefit of using SNN comes when computational effort and energy consumption are being compared. As can be seen from Table 4, the feed-forward SNN models of the system 100 have 50K training parameters which is ~7.5× less than that used in [Ramaswamy et al., 2021]—thus providing huge benefit in terms of memory and power requirement.

TABLE 4

| Dataset | Accuracy (in %) 5-FCV System 100 | 5-FCV Others | LOSO System 100 | LOSO Others | Training Parameters System 100 | Training Parameters Others | Computation Effort System 100 | Computation Effort Others | Approx. Power consumption SOP | Energy (μJ) |
|---|---|---|---|---|---|---|---|---|---|---|
| EEGMAT | 75 | 95[1] | 70 | 74[4] | 50K | 3.7M[1] | $o(10^3)$ | $o(2 \times 10^4)$[4] | 3 | 0.243 |
| STEW | 86 | 88[2] | 79 | 62[3] | 68K | 55K[3] | $o(7 \times 10^2)$ | $o(9 \times 10^5)$[2] $o(4 \times 10^4)$[3] | 16 | 0.331 |

As per [Mohammadi Farsani and Pazouki, 2020], the computational cost of transformer based EEG classifiers (such as [Siddhad et al., 2022]) are $o(n^2 \times d)$ where n is the length of input sequence and d is the input dimension (here, number of EEG channels). On the other hand, the same for SNN is $o(s \times d)$ where s is the total number of input spikes. For the case of STEW, n=2×128, d=14 and s=52 for window size=2 (refer Table 3). Consequently, the computational cost of [Siddhad et al., 2022] is approximately $o(9\times10^5)$ and that for [Pandey et al., 2020] is $o(4\times10^4)$ while same for feed-forward SNN is $o(52\times14)\approx o(7\times10^2)$, i.e. the system 100, provides a benefit in the range of $10^2$ to $10^3$ times. Similarly, for EEGMAT, d=23 197 and s=45, so computational cost of feed-forward SNN here is $o(45\times23)\approx o(10^3)$, whereas that for [Attallah, 2020] is $o(2\times10^4)$ i.e. 20 times more than the system 100.

The energy requirement of an SNN is directly proportional to the total number of synaptic operations (SOP) executed during runtime. As mentioned earlier, SOP is inherently dependent on the total number of spikes produced by the model, which includes the input spikes as well as the spikes occurring in the subsequent SNN layers during runtime. For example, during the experiment with EEGMAT dataset, it was observed that a total number of spikes=3000 on an average per sample data of window size 2 seconds. This 3000 spikes included the 45 input spikes (refer column 3 of Table 3) and the spikes (≈2955) in feed-forward SNN layer. So SOP can be calculated as 3000/(2×500 (sampling rate))=3. Similarly for STEW, SOP is found to be 16. Using this SOP values and the power consumption figures for Intel Loihi neuromorphic Chip™ [Davies et al., 2018], approximate power consumption in microJoule per inference which is pretty low and fits the power budget of wearable EEG devices.

Thus, the system and the method disclosed provide a real time in-situ cognitive load (CL) assessment approach using EEG signal targeted towards implementation on wearable EEG device. The experimental analysis and results depict that system 100 does not require artifact removal from the signal and works best for LOSO validation mode. The system disclosed has very low memory and energy footprint making it eligible for implementing on battery driven EEG devices.

USE CASES: 1. Online gaming 2. Online tuition/education: A user who is engaged on her mobile device/tablet for a gaming session or a tutor session is requested to wear a EEG wearable device such as Muse™, Emotiv™, neuroSky™, Zeo etc., In both the cases, the system 100 disclosed herein can be deployed on the Neuromorphic platform such as Intel Loihi™, Brainchip™, Akida™ that can be deployed on the wearable EEG devices or any wearable device such as hand gear wearable worn by a user (player/student). In the case of the wearable EEG device, it captures the multichannel raw EEG signal. The system 100 disclosed herein, which is deployed on the wearable device can then on the fly (in real time) processes the multichannel EEG for determining cognitive load level of the user. The cognitive load level can then be notified to the content provider of the game or tutorial provider, who can then change the difficulty level or interest level of the content so that user get more engaged and does not feel bored or down. For example, if the user loses consecutive rounds in a game, feels dejected and that reflects in his EEG signature, then the content can offer him less difficult game levels for him so that he starts winning and gets engaged again. Similarly in field of education case, if the student does not understand the content or finds it difficult for him, then the system can slow down the speed of the content so that the user can take more time to grasp it or can downgrade the difficulty level of the content so that it becomes easy to understand.

Thus, system 100 enables personalization of content for each individual user on the fly based on user response.

Conventional Cognitive Load (CL) level assessment approaches do not provide real time analysis and are not capable of running on EEG device itself due to their large memory footprint, power requirement etc. The system 100 disclosed herein can analyze EEG signal in-situ the wearable device itself as it consumes very less power and has less computational complexity as can be seen for the results section. This way, using conventional systems, one cannot measure the cognitive load "on the go" as it needs a constant power connection, need good network connection to send the data to cloud and run the large neural network model there in cloud to analyze the data. These problems can be overcome by the system 100 disclosed herein. The "content changing" facility as in use case above provides quicker/real time and good for user experience. Furthermore, the user can have more mobility as he is using the wearable EEG device that does not need a constant power supply and network connection. Everything can happen within the secure and private perimeter of the user himself.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means, and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method for cognitive load analysis, the method comprising:

receiving, via one or more hardware processors, a raw electroencephalogram (EEG) signal of a subject from a multichannel EEG set up for an observation window, wherein the subject is under continuous observation, and wherein the raw EEG signal is re-referenced to generate a re-referenced EEG signal of each channel using average of channels as reference;

simultaneously applying, via the one or more hardware processors, a Light-Weight-Lossless-Decoder less-Peak-based (LWDLP) encoding technique on the re-referenced EEG signal of each channel of the multi-channel EEG set up to generate a spike train to be consumed by a Spiking Neural Network (SNN) architecture, the LWLDP encoding technique comprising:

detecting a plurality of peaks in the re-referenced EEG signal using slope of the EEG signal in the time domain; and assigning a spike at each time instant associated with each peak among the plurality of detected peaks, and generate the spike train by retaining temporal information of the re-referenced EEG signal by making the inter-spike interval equal to inter-peak interval and retaining spatial information by encoding peaks as spikes; and classifying a cognitive load level of the subject by processing the spike train generated for each channel by the SNN architecture comprising, a spiking network implemented using one of a reservoir and a feed forward SNN, followed by a SNN classifier, wherein the reservoir or the feed forward SNN is selected in accordance with hardware constraints of an edge device, wherein the SNN architecture learns using backpropagation based supervised approach, wherein the spatial information and the temporal information are learnt by the SNN in form of neuronal activity and synaptic weights, and wherein post learning the SNN architecture applies an activation function on the neuronal activity for classifying the cognitive load level of the subject from among a plurality of predefined cognitive load levels using the SNN classifier.

2. The processor implemented method of claim 1, wherein number of output neurons in a last layer of the SNN classifier correspond to the number of classes associated with the plurality of predefined cognitive load levels.

3. The processor implemented method of claim 1, wherein the activation function is a sigmoid function.

4. A system for cognitive load analysis, the system comprising:

a memory storing instructions;

one or more Input/Output (I/O) interfaces;

one or more hardware processors coupled to the memory via the one or more I/O interfaces; and a neuromorphic platform implementing a Spiking Neural Networks (SNN) architecture, wherein the one or more hardware processors are configured by the instructions to:

receive a raw electroencephalogram (EEG) signal of a subject from a multichannel EEG set up for an observation window, wherein the subject is under continuous observation, and wherein the raw EEG signal is re-referenced to generate a re-referenced EEG signal of each channel using average of channels as reference;

simultaneously apply a Light-Weight-Lossless-Decoder less-Peak-based (LWDLP) encoding technique on the re-referenced EEG signal of each channel of the multichannel EEG set up to generate a spike train to be consumed by the SNN architecture, the LWLDP encoding technique comprising:

detecting a plurality of peaks in the re-referenced EEG signal using slope of the EEG signal in the time domain; and assigning a spike at each time instant associated with each peak among the plurality of detected peaks and generate the spike train by retains temporal information of the re-referenced EEG signal by making the inter-spike interval equal to inter-peak interval and retaining spatial information by encoding peaks as spikes; and classify a cognitive load level of the subject by processing the spike train generated for each channel by the SNN architecture comprising, a spiking network implemented using one of a reservoir and a feed forward SNN, followed by a SNN classifier, wherein the reservoir or the feed forward SNN is selected in accordance with hardware constraints of an edge device, wherein the SNN architecture learns using backpropagation based supervised approach, wherein the spatial information and the temporal information are learnt by the SNN in form of neuronal activity and synaptic weights, and wherein post learning the SNN architecture applies an activation function on the neuronal activity for classifying the cognitive load level of the subject from among a plurality of predefined cognitive load levels using the SNN classifier.

5. The system of claim 4, wherein number of output neurons in a last layer of the SNN classifier corresponds to the number of classes associated with the plurality of predefined cognitive load levels.

6. The system of claim 4, wherein the activation function is a sigmoid function.

7. One or more non-transitory machine-readable information storage mediums comprising one or more instructions which when executed by one or more hardware processors cause:

receiving, a raw electroencephalogram (EEG) signal of a subject from a multichannel EEG set up for an observation window, wherein the subject is under continuous observation, and wherein the raw EEG signal is re-referenced to generate a re-referenced EEG signal of each channel using average of channels as reference;

simultaneously applying, a Light-Weight-Lossless-Decoder less-Peak-based (LWDLP) encoding technique on the re-referenced EEG signal of each channel of the multichannel EEG set up to generate a spike train to be consumed by a Spiking Neural Network (SNN) architecture, the LWLDP encoding technique comprising:

detecting a plurality of peaks in the re-referenced EEG signal using slope of the EEG signal in the time domain; and assigning a spike at each time instant associated with each peak among the plurality of detected peaks, and generate the spike train by retaining temporal information of the re-referenced EEG signal by making the inter-spike interval equal to inter-peak interval and retaining spatial information by encoding peaks as spikes; and classifying a cognitive load level of the subject by processing the spike train generated for each channel by the SNN architecture comprising, a spiking network implemented using one of a reservoir and a feed forward SNN, followed by a SNN classifier, wherein the reservoir or the feed forward SNN is selected in accordance with hardware constraints of an edge device, wherein the SNN architecture learns using backpropagation based supervised approach, wherein the spatial information and the temporal information are learnt by the SNN in form of neuronal activity and synaptic weights, and wherein post learning the SNN architecture applies an activation function on the neuronal activity for classifying the cognitive load level of the subject from among a plurality of predefined cognitive load levels using the SNN classifier.

8. The one or more non-transitory machine-readable information storage mediums of claim 7, wherein number of output neurons in a last layer of the SNN classifier correspond to the number of classes associated with the plurality of predefined cognitive load levels.

9. The one or more non-transitory machine-readable information storage mediums of claim 7, wherein the activation function is a sigmoid function.

* * * * *